United States Patent [19]
Schrock et al.

[11] Patent Number: 6,121,473
[45] Date of Patent: Sep. 19, 2000

[54] ASYMMETRIC RING-CLOSING METATHESIS REACTIONS

[75] Inventors: Richard R. Schrock, Winchester; John B. Alexander, Somerville, both of Mass.

[73] Assignee: Massachusetts Institute of Technology, Cambridge, Mass.

[21] Appl. No.: 09/026,057

[22] Filed: Feb. 19, 1998

[51] Int. Cl.$^7$ .................................................. G07F 11/00
[52] U.S. Cl. ............................................. 556/57; 556/63
[58] Field of Search .......................................... 556/57, 63

[56] References Cited

U.S. PATENT DOCUMENTS

| | | |
|---|---|---|
| 4,654,462 | 3/1987 | Basset et al. . |
| 4,681,956 | 7/1987 | Schrock . |
| 5,516,953 | 5/1996 | Feldman et al. . |
| 5,639,900 | 6/1997 | Bell et al. . |
| 5,675,051 | 10/1997 | Chauvin et al. . |
| 5,739,396 | 4/1998 | Trost et al. . |
| 5,747,409 | 5/1998 | Commereuc . |
| 5,750,815 | 5/1998 | Grubbs et al. . |

OTHER PUBLICATIONS

K.M. Totland et al., "Ring Opening Metathesis Polymerization with Binaphtholate or Biphenolate Complexes of Molybdenum", Macromolecules, vol. 29, No. 19, pp. 6114–6125, 1996.

R. O'Dell et al., "Polymerization of Enantiomerically Pure 2,3–Dicarboalkoxynorbornadienes and 5,6–Disubstituted Norbornes by Well–Characterized Molybdenum Ring-Opening Metathesis Polymerization Initiators. Direct Determination of Tacticity in Cis, Highly Tactic and Trans, Highly Tactic Polymers", J.Am.Chem.Soc., vol. 116, No. 8, pp. 3414–3423, 1994.

D.McConville et al., "Synthesis of Chiral Molybdenum ROMP Initiators and All–Cis Highly Tactic Poly(2, 3–(R)$_2$norbornadiene) (R =CF$_2$ or CO$_2$Me)", J.Am.Chem. Soc., vol. 115, No. 10,pp. 4413–4414, 1993.

O. Fujimura et al., "The Synthesis of Cyclic Enol Ethers via Molybdenum Alkylidene–Catalyzed Ring–Closing Metathesis", J.Org.Chem., vol. 59, No. 15, pp. 4029–4031, 1994.

O.Fujimura and R. H. Grubbs, "Asymmetric Ring–Closing Metathesis Catalyzed by Chiral Molybdenum Alkylidene Complexes", J.Org.Chem., vol. 63, No. 3, pp. 824–832, 1998.

G.C. Fu and R.H. Grubbs, "Synthesis of Nitrogen Heterocycles via Catalytic Ring–Closing Metathesis of Dienes", J.Am.Chem.Soc., vol. 114, No. 18, pp. 7324–7325, 1992.

G.C. Fu and R.H. Grubbs, "The Application of Catalytic Ring–Closing Olefin Metathesis to the Synthesis of Unsaturated Oxygen Heterocycles", J.Am.Chem.Soc., vol. 114, pp. 5426–5427, 1992.

J.A. Heppert et al., "Asymmetric Alyklidene and Oxo Complexes of Tungsten (VI)", Organometallics, vol. 12, No. 7, pp. 2565–2572, 1993.

O.Fujimura and R.H. Grubbs, "Asymmetric Ring–Closing Metathesis: Kinetic Resolution Catalyzed by a Chiral Molybdenum Alkylidene Complex", J.Am.Chem.Soc., vol. 118, No. 10, pp. 2499–2500, 1996.

O.Fujimura et al., "Synthesis of New Chiral Ligands and Their Group VI Metal Alkylidene Complexes", Organometallics, vol. 15, No. 7, pp. 1865–1871, 1996.

M. Schuster and S. Blechert, "Olefin Metathesis in Organic Chemistry", Angew.Chem.Int.Ed.Engl. vol. 36, pp. 2037–2056, 1997.

Z.Xu et al., "Applications of Zr–Catalyzed Carbomagnesation and Mo–Catalyzed Macrocyclic Ring Closing Metathesis in Asymmetric Synthesis, Enantioselective Total Synthesis of Sch 38516 (Fluvirucin B$_1$)", J.Am.Chem.Soc., vol. 119, No. 43, pp. 10302–10316, 1997.

J.Bao et al., "Synthesis, Resolution, and Determination of Absolute Configuration of a Vaulted 2.2'—Binaphthol and a Vaulted 3.3'–Biphenanthrol (VAPOL)", J.Am.Chem.Soc., vol. 118, No. 14, pp. 3392–3405, 1996.

Schrock et al., "Exploring Factors that Determine Cis/Trans Structure and Tacticity in Polymers Prepared by Ring–Opening Metathesis Ploymerization with Initiators of the Type syn–and anti–Mo(NAr)(CHCMe$_2$Ph)(OR)$_2$. Observation of a Temperature–Dependent Cis/Trans Ratio," Macromolecules, vol. 28, No. 17, pp. 5933–5940, 1998.

La et al., "Mo–Catalyzed Asymmetric Synthesis of Dihydrofurans. Catalytic Kinetic Resolution and Enantioselective Desymmetrization through Ring–Closing Metathesis," J. Am. Chem. Soc., vol. 120, No. 37, pp. 9720–9721, 1998.

Alexander et al., "Catalytic Enantiioselective Ring–Closing Metathesis by a Chiral Biphen–Mo Complex," J. Am. Chem. Soc., vol. 120, No. 16, pp. 4041–4042, 1998.

Primary Examiner—Paul J. Killos
Attorney, Agent, or Firm—Wolf, Greenfield & Sacks, P.C.

[57] ABSTRACT

A composition and method for the catalytic conversion of a racemic mixture of dienes to a cyclic olefin by a ring-closing metathesis (RCM) reaction are disclosed. The composition, a transition metal complex with an M=C reaction site, contains a bidentate dialkoxide of at least 80% optical purity. Because the M=C reaction site is of a sufficient shape specificity, conferred in part by the dialkoxide of sufficient rigidity and a M=N—R$^1$ site, reacting the composition with a mixture of two enantiomeric dienes results in an olefin metathesis product that has at least a 50% enantiomeric excess of one enantiomer in the mixture. A method is also provided for reacting a composition with a racemic diene mixture to generate a metathesis product that has an enantiomeric excess of at least 50%.

40 Claims, 2 Drawing Sheets

ASYMMETRIC RING-CLOSING METATHESIS REACTIONS

This invention was made with government support under Grant Numbers CHE-9700736 and 9122827-CHE, awarded by the National Science Foundation. The government has certain rights in the invention.

FIELD OF INVENTION

The present invention describes the catalytic conversion of a racemic mixture of dienes to a cyclic olefin by a ring-closing metathesis (RCM) reaction. At 50% conversion of the diene mixture, the product olefin has an enantiomeric excess of at least 50%. The catalyst contains a reactive M=C site, an amido ligand and a chiral linked dialkoxide ligand to promote enantioselectivity through kinetic resolution, and M is molybdenum or tungsten.

BACKGROUND OF THE INVENTION

The formation of carbon—carbon bonds remains among the most important reactions in synthetic organic chemistry. Consequently, the development of transition metal catalyzed carbon—carbon bond formation represented a significant advance in organic synthesis. One reaction involving transition metal catalyzed carbon—carbon formation is olefin metathesis. Olefin metathesis can be defined conceptually as a mutual exchange of alkylidene units between two olefins involving both the formation and cleavage of carbon—carbon double bonds. Transition metal ion catalysts allow this reaction to proceed in a facile manner through a [2+2] cycloaddition between an M=C center and a carbon—carbon double bond. When two olefin groups are located on the same molecule and are subjected to olefin metathesis conditions, a ring-closing metathesis (RCM) reaction can occur in which a series of olefin metathesis reactions produce a cyclic olefin. Ring-closing metathesis is most facile for 5–7 membered ring systems because of the low ring strain afforded by these compounds. Ruthenium and molybdenum alkylidene complexes have proven capable of ring closing dienes having a variety of functional groups.

RCM reactions are generally plagued by undesirable reactions that compete with ring formation, such as acyclic diene metathesis and ring opening metathesis. The former reaction involves polymer formation through the metathesis of terminal dienes whereas the latter reaction comprises metathesis reactions of the ring-closed cyclic olefin. These competing reactions can be circumvented, for example, by performing the reactions under dilute conditions, optimizing ring sizes and utilizing hindered olefin substrates. The latter strategy is also useful for directing the initial reaction of the metal alkylidene towards one olefinic site in a diene over the other olefinic group.

The development of asymmetric ring closing metathesis has considerable potential as a powerful synthetic tool for the preparation of ring structures of defined stereosymmetry. For example, a logical application of asymmetric RCM is the synthesis of natural products which contain varying sizes of ring systems having pendant functional groups of specific stereosymmetry. U.S. Pat. No. 5,516,953 discloses a process for the preparation of optically active cycloolefins catalyzed by molybdenum and tungsten complexes. This process requires that substrate be initially isolated as an optically active diene. Olefin metathesis is catalyzed by molybdenum and tungsten halide or oxide complexes that may also contain alkoxide or amido ligands. In some instances, a tin, lead, aluminum, magnesium or zinc complex cocatalyst may be required.

U.S. Pat. No. 4,654,462 describes a process for olefin metathesis by a tungsten complex containing two phenoxy groups, a halogen atom, an alkyl radical and a carbene. Stereoselectivity is reported sufficient to control cis/trans isomerization in the metathesis of pure cis or trans olefins.

Only recently, the first report of an asymmetric RCM reaction involving the interaction of a chiral catalyst with a racemic substrate mixture was reported by Grubbs et al. *J. Am. Chem. Soc.* 1996, 118, 2499, *Organometallics* 1996, 15, 1865. A racemic diene substrate was added to a molybdenum alkylidene amido catalyst containing a dialkoxide ligand. At various conversion levels of the starting mixture, the enantiomeric excess of the unreacted diene mixture was analyzed, resulting in enantiomeric excess values of up to 48%. The enantiomeric excess of the ring-closed product was not reported. It was proposed that the dialkoxide had a rigid structure suitable to promote the transfer of asymmetry.

There remains a fundamental need for the synthesis of optically pure products by using asymmetric ring-closing metathesis reactions. In a recent review article, Blechert et al. discuss the state of the art relating to asymmetric RCM reactions, maintaining that "In light of the e.e. [enantiomeric excess] values obtained to date, synthetic applications of this process are currently not envisioned." *Angew. Chem., Int. Ed. Engl.* 1997, 36, 2036. Asymmetric processes only begin to show promise industrially when achieving enantiomeric excess values of at least 80%.

It remains a challenge to design a metal catalyst that can produce ring structures of various sizes and pendant functional groups while achieving high enantioselectivity.

SUMMARY OF THE INVENTION

In one illustrative embodiment of the present invention, a composition is provided having the structure:

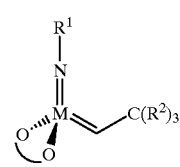

I

The composition has a chiral dialkoxide ligand, denoted by

wherein the dialkoxide is of at least 80% optical purity. A

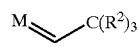

reaction site is of sufficient shape specificity, defined in part by the dialkoxide of sufficient rigidity and a M=N—R¹ site to cause a mixture of two enantiomeric olefins to react with an M=C center of the

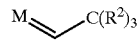

reaction site at different rates. The reaction is an olefin metathesis reaction and the product has at least a 50% enantiomeric excess of one enantiomer present in the original mixture. M is a metal ion, preferably molybdenum or tungsten.

In one embodiment of the invention, the group of atoms defining the shortest chemical bond pathway linking the oxygen atoms in

contains at least four atoms. In another illustrative embodiment of the present invention,

comprises the structure:

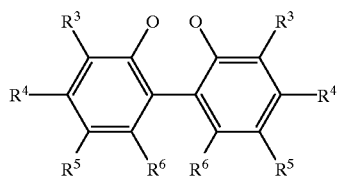

II

The chiral dialkoxide transfers asymmetry to the composition such that the composition is at least 80% optically pure.

In another embodiment of the present invention, a method is provided wherein a diene mixture of enantiomers is reacted with the M=C center of the above-mentioned composition. The method involves allowing a first enantiomer of the mixture to metathesize at M to an extent greater than a second enantiomer to form a product that has an enantiomeric excess of at least 50%. The metathesizing step occurs catalytically.

One aspect of the invention provides a method which includes a step of adding the racemic diene mixture to produce a ring-closed metathesis compound having an enantiomeric excess of at least 50% at 50% conversion of the diene mixture. Moreover, the enantiomeric excess of an enantiomer in the unreacted diene mixture is at least 50% at 50% conversion. The method allows 50% conversion of the racemic diene mixture to be achieved within a time of at least 5 minutes.

In another illustrative embodiment of the present invention, the diene comprises the structure:

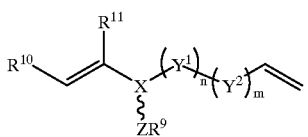

III

The diene contains one unsubstituted olefin group and one hindered olefin group to direct the initial metathesis towards the unsubstituted end. Reaction of the diene with the composition results in the formation of a ring-closed compound. The diene has a stereocenter and is available as a racemic mixture.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

Figure 1:
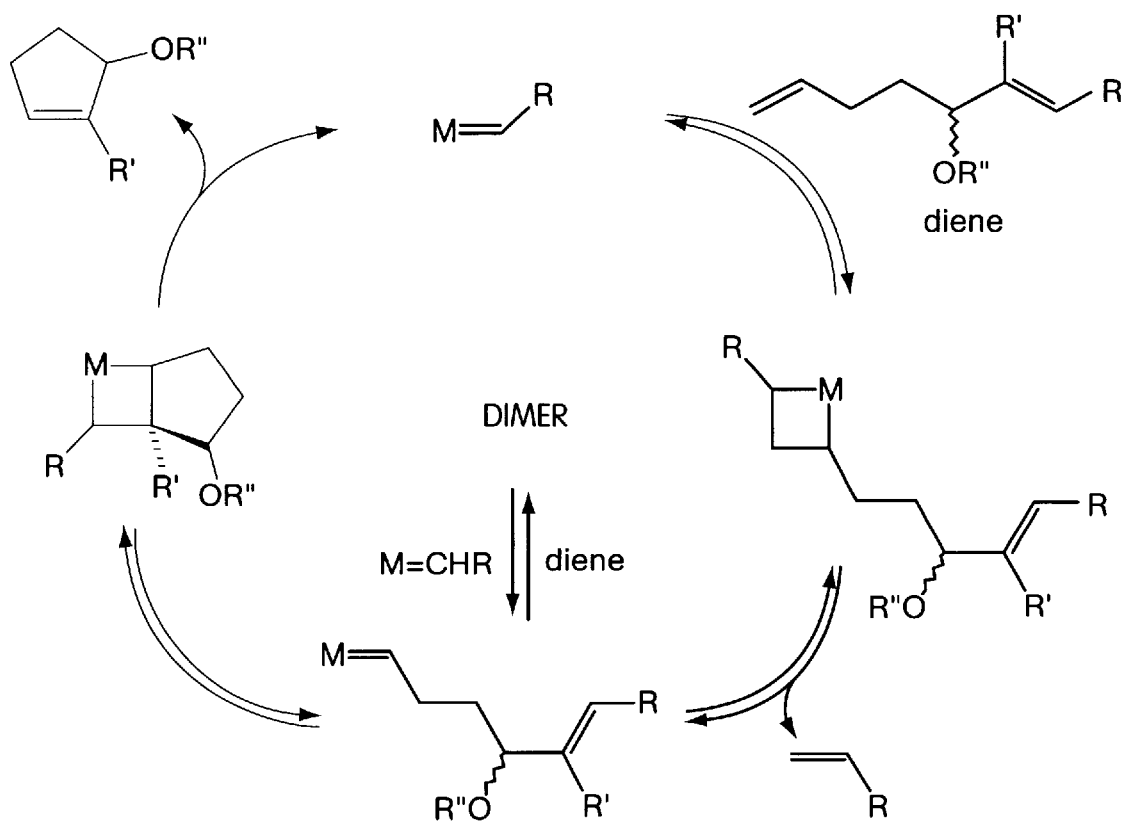
FIG. 1 depicts a proposed mechanism for a ring-closing metathesis catalytic cycle, illustrating the reaction intermediates.

The present invention provides an olefin metathesis catalyst. In one illustrative embodiment of the present invention, a composition is provided comprising the structure:

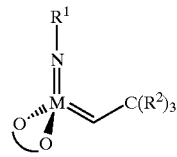

I

The metal ion, M, is preferably molybdenum or tungsten. The composition has a chiral dialkoxide, denoted by

The term "chiral" herein refers to a molecule that is not superimposable with its mirror image. The resulting nonsuperimposable mirror images are known as "enantiomers" and are labeled as either an (R) enantiomer or an (S) enantiomer. Because enantiomers contain chiral centers, they are included in a specific type of isomerism called "stereoisomerism." A molecule such as $CX_2WY$ would not have enantiomers; the replacement of one X by another group Z, however, would lead to one enantiomer; conversely the replacement of the other X by Z would lead to the other enantiomer. From this viewpoint, the X atoms in $CX_2WY$ are not equivalent and are defined as "enantiotopic". A "prochiral molecule" is a molecule such as $CX_2WY$ that contains two enantiotopic atoms or groups, such as the X atoms in $CX_2WY$. "Chiral molecules" as used herein also includes by definition prochiral molecules.

$R^1$ and $R^2$ can be the same or different, and each is selected from the group consisting of $C_1-C_{12}$ alkyl, heteroalkyl, aryl, heteroaryl and adamantyl. Preferably, $R^1$ is 2,6-dimethylphenyl, 2,6-diethylphenyl or 2,6-diisopropylphenyl and $R^2$ is methyl, ethyl or phenyl.

An "alkoxide" ligand herein refers to a ligand prepared from an alcohol, in that removing the hydroxyl proton from an alcohol results in a negatively charged alkoxide. The alkoxide of the present invention is a linked, bidentate dialkoxide ligand. Moreover, the dialkoxide is chiral and can exist as one of two enantiomers. Each dialkoxide enantiomer interacts with plane-polarized light differently, in that this plane is rotated by both enantiomers to the same extent but in opposite directions. If a sample contains only one enantiomer, a measurement of the sample's optical activity would reveal an "optically pure" compound. The chiral dialkoxide of the present invention is of at least 80% optical purity in that the dialkoxide sample contains 90% of one enantiomer and 10% of the other. The dialkoxide preferably is at least 90% optically pure, more preferably at least 95% optically pure, and more preferably still at least 99% optically pure.

It is a feature of the present invention that a catalytic composition is provided having a dialkoxide of sufficient rigidity such that, in conjunction with an M=N—$R^1$ site, the combination of the dialkoxide and the M=N—$R^1$ site in part confers a shape specificity to a

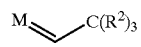

reaction site where the composition reacts with an olefin. This shape specificity, imparted by rigidity of the dialkoxide ligand, is sufficient to allow a mixture of two enantiomeric olefins to react with a M=C center of the

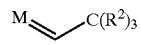

reaction site at different rates. That is, the invention provides a catalyst designed to have shape specificity sufficient to differentiate between enantiomers of a reactant by sterically interacting with one enantiomer almost exclusively or exclusively. A means to achieve a preference for one enantiomer over the other, or enantiomeric selectivity, is kinetic resolution. Enantiomeric selectivity by kinetic resolution involves reducing the steric interactions in the transition state of the reaction of the substrate at the catalyst such that the transition state involving one enantiomer is of lower energy than the transition state of the other enantiomer. Consequently, the term shape specificity in the present invention refers to the shape of an M=C reaction site in the transition state, as formed by the surrounding ligands, such that upon reaction of the substrate with the metal compound, one enantiomer "fits into" the binding site with less steric interaction than the other enantiomer. The transition state energy is lower for the enantiomer with a better "fit" or shape specificity over the other.

A method to screen for dialkoxides having sufficient rigidity for shape specificity purposes involves obtaining an enantiomeric mixture of a test dialkoxide, isolating one enantiomer and measuring a specific rotation. A dialkoxide of sufficient rigidity would provide a specific rotation as opposed to reverting back to an enantiomeric mixture.

Generally, two enantiomeric olefins can react with an M=C center catalytically to form an olefin metathesis product. Olefin metathesis is defined conceptually as a mutual exchange of alkylidene units between two olefins, as illustrated in eq 1:

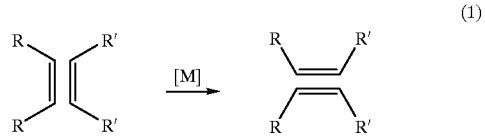

(1)

This reaction is catalyzed by a metal complex, denoted in the equation as [M]. In the present invention, the metal complex is a chiral metal complex including a chiral metal center that can transform olefin substrates (reactants) into optically pure products. Typically, the substrate is a racemic mixture, the term "racemic" referring to a mixture containing an equal ratio of (R) and (S) enantiomers. The chiral metal complex of the invention can function as an asymmetric catalyst and simplifies the reaction process due to its ability to resolve a racemic mixture in generating a product of high enantioselectivity, or optical purity. The extent of optical purity of a product is gauged by the "enantiomeric excess" or "e.e." of the product mixture. The enantiomeric excess is the difference between the percent of the majority enantiomer minus the percent of the minority isomer, as represented by the equation $[([R]-[S])/([R]+[S])] \times 100$ in which [R] and [S] refers to concentration of the (R) and (S) enantiomer respectively. For example, if a mixture contains a 50% e.e. of the (R) configuration, the mixture contains 75% of the (R) configuration and 25% of the (S) configuration. In the present invention, the a mixture of the two enantiomeric olefins react with the M=C center at different rates to generate an olefin metathesis product that has at least a 50% enantiomeric excess of one enantiomer present in the mixture, preferably at least 85%, more preferably at least 90% and more preferably still at least 95%.

In one embodiment of the invention, a species as defined above is provided including a dialkoxide comprising two linked oxygen atoms such that the group of atoms defining the shortest chemical bond pathway between the two oxygen atoms has at least four atoms. For example, the four atoms can be four unsaturated atoms which confer rigidity to an organic group because they possess less degrees of freedom than a saturated atom. Examples of unsaturated carbon atoms are found in alkene, alkyne or aryl substituents.

The present invention also provides a dialkoxide, which can comprise

in I, comprising the structure:

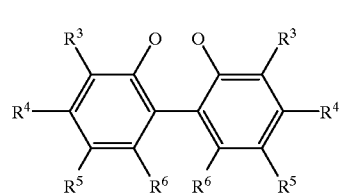

II wherein $R^3$–$R^6$ can be the same or different, and each is selected from the group consisting of hydrogen, alkyl, alkenyl, alkynyl, cycloalkyl, cycloalkenyl, cycloalkynyl, aryl, alkaryl, aralkyl and optionally interrupted or terminated by N, O, P, S, heteroalkyl, heteroaryl, carbonyl, acyl, acyloxy, —CHO, —COO$R^7$, —CO$_2$C(R$^7$)$_3$, —CONC(R$^7$)$_2$, cyano, NO$_2$, alkyloxy, aryloxy, hydroxy, hydroxyalkyl, amino, alkylamino, dialkylamino, arylamino, diarylamino, —NR$^7$COR$^8$, thioalkyl, thioaryl, —SO$_2$R$^7$, —SOR$^7$, —SO$_2$OR$^7$, F, Cl, Br, I; R$^7$ and R$^8$ can be the same or different, and is selected from the group consisting of hydrogen, C$_1$–C$_{12}$ alkyl, C$_1$–C$_{12}$ heteroalkyl, aryl, heteroaryl, hydroxyl, F, Cl, Br and I; and any two R groups where possible can combine to form a closed ring system selected from the group consisting of aryl, heteroaryl, substituted aryl, biaryls, and substituted biaryls. Preferably, $R^3$–$R^6$ can be the same or different and each is selected from the group consisting of $C_1$–$C_{12}$ alkyl, heteroalkyl, aryl, heteroaryl, optionally interrupted or terminated by N or O, and any two R groups where possible can combine to form a closed ring system selected from the group consisting of aryl, heteroaryl, substituted aryl, biaryls and substituted biaryls. More preferably, $R^3$ is i-propyl, t-butyl, cyclohexyl, t-octyl, $R^4$ is hydrogen or $C_1$–$C_2$ alkyl, $R^5$ is hydrogen or $C_1$–$C_2$ alkyl, and $R^6$ is methyl.

The chirality of the dialkoxide according to this embodiment results from steric interactions of the $R^6$ groups maintaining a rotational orientation of the phenyl groups about the biaryl bond such that the two phenyl groups are non-planar with respect to each other. In this manner, the dialkoxide of this embodiment confers chirality to a metal complex, as illustrated below:

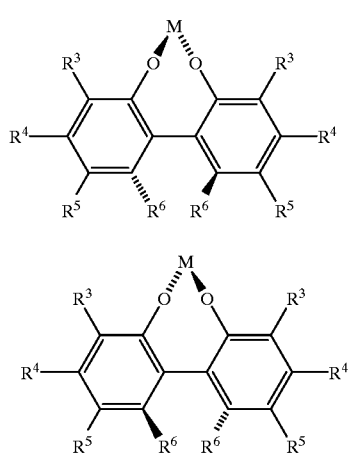

In a particularly preferred embodiment, the dialkoxide of the invention confers chirality to the metal complexes IV and V through the interaction between $R^6$ methyl groups of dialkoxide II. The present invention provides a composition that is a chiral metal complex in which the composition is at least 80% optically pure, preferably at least 90% optically pure, more preferably at least 95% optically pure, and more preferably still at least 99% optically pure.

While not wishing to be bound by any theory, specificity of the catalyst of the invention where the alkoxide is II is due to the following: Upon binding the dialkoxide to a metal center, a seven-membered metallacycle results. This configuration allows bulky functional groups in the $R^3$ positions to point towards the general direction of the M=C reaction center, aiding in providing shape specificity to the M=C reaction site.

In another embodiment of the present invention, the olefin metathesis reaction is a ring-closing metathesis (RCM) reaction in which a ring-closed compound is produced. Preferably, the ring-closed compound is a cyclic olefin. To obtain the cyclic product, the substrate must be a diene to achieve ring-closing through two subsequent olefin metathesis reactions. The diene source of the present invention is a racemic diene mixture where the diene is of from about 4 to about 18 carbons in length, preferably from about 7 to about 12 carbons in length. The double bonds of the diene are separated by enough distance that a ring can be formed. Other considerations for diene selection are described below. Exposing the composition of the present invention to the racemic diene mixture produces a ring-closed compound with high enantioselectivity. This high enantioselectivity is demonstrated at 50% conversion of the racemic diene mixture, in which the ring-closed compound has an enantiomeric excess of at least 50%, preferably at least 85%, more preferably at least 90% and more preferably still at least 95%. The enantiomeric excess of the remaining unreacted diene can also be measured. At 50% conversion of the racemic diene mixture, the unreacted diene has an enantiomeric excess of at least 50%, more preferably at least 85%.

Another aspect of the invention provides a method comprising reacting the composition, I, of the present invention with a diene. In another embodiment of the invention, the method comprises reacting an enantiomeric diene mixture with the composition of the present invention and allowing a first enantiomer of the mixture to metathesize at the metal ion, M, to an extent greater than a second enantiomer of the mixture. The resulting product has an enantiomeric excess of at least 50%. The composition is at least 80% optically pure, preferably at least 90% optically pure, more preferably at least 95% optically pure and more preferably still 99% optically pure. Preferably, the metal ion is molybdenum or tungsten.

In another embodiment of the invention, addition of the diene mixture to the compound produces a ring-closed compound. Preferably the ring-closing reaction is a ring-closing metathesis reaction. In this embodiment the enantiomeric diene mixture of the present invention comprises the structure:

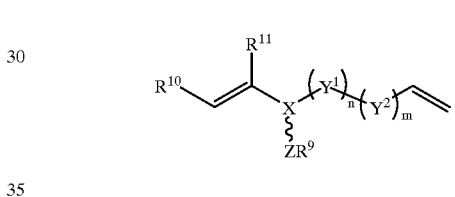

The method of reacting the diene with the composition can optionally include the step of dissolving the composition in a solvent before adding the diene.

The extent of substitution on the respective diene olefinic groups can be important in preventing undesirable side reactions which would decrease metathesis activity and product selectivity. Due to steric demands, an unsubstituted olefin reacts with an M=C bond at a faster rate than a substituted olefin. A diene containing two terminal unsubstituted olefin groups, however, will react with M=C reaction sites to generate polymers by the well-known acyclic diene metathesis reaction. If desirable, the rate of metathesis can be decreased to the extent that polymer formation is negligible typically by substituting the hydrogen atoms on the second olefin group with bulkier substituents such as methyl, ethyl, or the like, for example the $R^{10}$ or $R^{11}$ groups in the above-mentioned structure.

Referring to FIG. 1, a proposed mechanism for an RCM catalytic cycle involving diene III is shown, illustrating the reasons for the preferred diene structure according to this embodiment. At the top of FIG. 1, a complex containing a M=C reaction site reacts with a diene structure of the present invention at the unsubstituted terminal olefin site. A metallacyclobutane intermediate results that subsequently releases an olefin and a metal complex containing the reacted diene group. This complex can either react with the substituted olefin intramolecularly or with another diene intermolecularly at its unsubstituted terminal olefin site. The latter reaction is unproductive, however, in that the resulting product dimer is unstable and upon reaction with a M=C reaction site, reverts back to the M=C complex. The intramolecular reaction produces a bicyclic compound comprising a metallacyclobutane fused to another closed-ring structure which consequently transforms into cyclic olefin product and a complex containing a M=C reaction site. Yet another undesirable side reaction is metathesis of the cyclic olefin product with the M=C reaction site through a ring-opening metathesis process. Again, designing the diene to produce a cyclic olefin that affords minimal ring strain or that contains a relatively hindered olefin may contribute to a decrease in rate of the ring-opening reaction.

In embodiments of the present invention in which the diene is III, X is selected from the group consisting of $CR^{12}$, N or P. $Y^1$, $Y^2$ and Z can be the same or different and each is selected from the group consisting of $CR^{12}R^{13}$, $NR^{12}$, O or S. When a diene contains main group elements at the X, $Y^1$ or $Y^2$ sites, heterocyclic products can be formed. $R^{10}$ and $R^{11}$ can be the same or different, and each is selected from the group consisting of hydrogen, alkyl, alkenyl, alkynyl, cycloalkyl, cycloalkenyl, cycloalkynyl, aryl, alkaryl, aralkyl and optionally interrupted or terminated by N, O, P, S, heteroalkyl, heteroaryl, carbonyl, acyl, acyloxy, —CHO, —COOR$^2$, —CO$_2$C(R$^{12}$)$_3$, —CONC(R$^{12}$)$_2$, cyano, NO$_2$, alkyloxy, aryloxy, hydroxy, hydroxyalkyl, amino, alkylamino, dialkylamino, arylamino, diarylamino, —NR$^{12}$COR$^{13}$, thioalkyl, thioaryl, —SO$_2$R$^2$, —SOR$^{12}$, —SO$_2$OR$^{12}$, F, Cl, Br, I. $R^9$, $R^{12}$ and $R^{13}$ can be the same or different, and each is selected from the group consisting of hydrogen, $C_1$–$C_{12}$ alkyl, $C_1$–$C_{12}$ heteroalkyl, aryl, heteroaryl, hydroxyl, alkylsilyl, arylsilyl, alkarylsilyl, F, Cl, Br and I. Any two R groups, where possible, can combine to form a closed ring system selected from the group consisting of aryl, heteroaryl, substituted aryl, biaryls, and substituted biaryls. The value "n+m" is at least 2. Preferably, n+m ranges from 2 to 4. More preferably, n+m=2. Where n+m=2, the cyclic product is a five-membered ring. Increasing n or m provides for the possibility of forming larger ring systems. Preferably, $Y^1$, $Y^2$ and Z can be the same or different and each is selected from the group consisting of $CR^{12}R^{13}$, $NR^{12}$, O or S. $R^{10}$, $R^{11}$, $R^{12}$, and $R^{13}$ can be the same or different and each is selected from the group consisting of $C_1$–$C_{12}$ alkyl, heteroalkyl, aryl or substituted aryl and $R^9$ is selected from the group consisting $C_1$–$C_{12}$ alkyl, heteroalkyl, aryl or substituted aryl, alkylsilyl, arylsilyl, and alkylarylsilyl. More preferably, X is CH, $Y^1$ and $Y^2$ each are CH$_2$, and $ZR^9$ is selected from the group consisting of acetate, t-butylacetate, trifluoroacetate, and trialkylsilyloxide.

In another embodiment of the invention, a method is provided that generates a ring-closed metathesis compound from a racemic diene mixture such that at 50% conversion of the racemic diene mixture, the product has an enantiomeric excess of at least 50%, preferably 85%, more preferably at least 90% and more preferably still at least 95%. The optical purity of the unreacted diene can also be analyzed and at 50% conversion of the racemic diene mixture, the enantiomeric excess of the unreacted diene is at least 50%, preferably at least 85%. In another embodiment of the invention, a step of adding the diene mixture to the composition results in 50% conversion of the racemic diene mixture within a time of at least 5 minutes.

The present invention also provides a method to achieve enantiomeric selectivity through kinetic resolution. As discussed previously, kinetic resolution can be achieved when a transition state involving the reaction of the M=C center with one enantiomer is of lower energy than a transition state involving the other enantiomer. This lowered transition state energy arises from the shape specificity of the binding site for that one particular enantiomer, the end result being that the one enantiomer undergoes RCM at a faster rate than the other enantiomer. The reaction rate is dependent on the rate constant, in which the rate constant of a reaction involving the (S) enantiomer is labeled as $k_s$, and the rate constant of a reaction involving the (R) enantiomer is denoted by $k_r$, in equations 2 and 3, respectively. For example, to obtain a product mixture containing predominantly the (R) enantiomer, $k_r$ should be sufficiently greater than $k_s$. The present invention provides sufficient kinetic resolution to obtain, for example, the (R) enantiomer of the product such that adequate optical purity, as defined above, is achieved when the value of $S=k_r/k_s$ (eq 4) is at least 10, preferably at least 25.

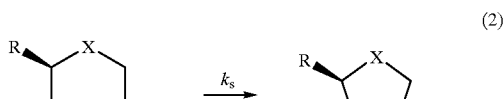

(2)

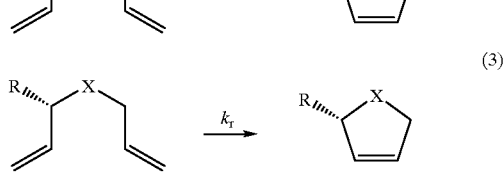

(3)

Relative Rate = $S = k_r/k_s$ (4)

The function and advantage of these and other embodiments of the present invention will be more fully understood from the examples below. The following examples are intended to illustrate the benefits of the present invention, but do not exemplify the full scope of the invention.

EXAMPLE 1

Preparation and Resolution of t-Bu$_2$Me$_4$BiphenH$_2$

The compound t-Bu$_2$Me$_4$BiphenH$_2$ (1) was prepared from commercially available 3,4-dimethylphenol

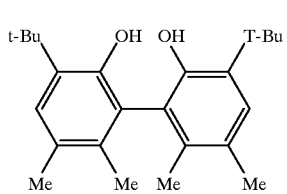

1 in two steps. The phenol was alkylated at 65° C. under 2 atmospheres of isobutylene and a catalytic amount of sulfuric acid. The crude trialkylphenol was oxidized directly to the biphenol with potassium chromate in hot acetic acid. The overall yield from 3,4-dimethyl phenol was ~50%.

The biphenol was resolved by selective crystallization using similar conditions to those reported by Wulff et al. to resolve a "vaulted" 2,2'-binaphthol and a vaulted 3,3'-biphenanthrol. The enantiomerically pure (−) biphenol was isolated employing (−) cinchonidine as the base. The specific rotation of the resolved biphenol was determined; [α]D=−53.0° (c=0.352, THF). All transition metal catalysts listed herein in the examples contain the (−) biphenol enantiomer.

EXAMPLE 2

Mo(N-2,6-i-Pr$_2$C$_6$H$_3$)(CHCMe$_2$Ph)[(−)-t-BU$_2$MeBiphen] (2)

The compound (−) t-Bu$_2$Me$_4$BiphenH$_2$ (1) (500 mg, 1.16 mmol), was dissolved in THF (10 mL). Potassium hydride (2.1 eq, 98 mg) was added portionally as a solid. After 24 hours, additional THF (10 mL) was added and the suspension was filtered through celite. The THF solution was cooled to −30° C. Mo(NAr)(CHCMe$_2$Ph)(OTf)$_2$ (dimethoxyethane) (1.2 equiv, 1070 mg, 1.4 mmol) was dissolved in THF (15 mL) and the solution was cooled to −30° C. The THF solutions were combined and allowed to stir at room temperature for one hour and then stored overnight at −30° C. The volatiles were removed in vacuo and the red powder extracted with pentane. The slurry was filtered through celite to remove the potassium triflate. Removing the pentane yielded a spongy orange solid. Crystallization from concentrated diethyl ether gave 475 mg product in the first two crops (49%). $^1$H NMR (C$_6$D$_6$) δ 10.98 (s, 1H,=CHR), 7.42 (m, 3H, biph+Ph), 7.16 (m, 3H, biph+Ph), 7.05 (t, 1H, Ph), 6.92 (s, 3H, NAr), 3.70 (heptet, J$_{HH}$=7.0 Hz, 2H, CHMe$_2$), 2.132 (s, 3H), 2.147 (s, 3H), 1.850 (s, 3H), 1.739 (s, 3H), 1.662 (s, 3H) {2.13–1.66 ppm are 4 biphMe's and one CMe2Ph}, 1.595 (s, 9H, t-Bu), 1.542 (s, 9H, t-Bu), 1.145 (d, J$_{HH}$=7.0 Hz, 6H, CHMe$_2$), 1.133 (s, 3H, CMeMePh), 0.906 (d, J$_{HH}$=7.0 Hz, 6H, CHMe$_2$). $^{13}$C{$^1$H} NMR (C$_6$D$_6$)δ 277.07 (d, J$_{CH}$=123 Hz), 155.4, 154.5, 154.3, 151.3, 146.8, 140.0, 138.0, 136.5, 135.7, 132.0, 131.1, 130.9, 130.6, 129.6, 128.2, 127.9, 126.3, 123.8, 53.71, 35.95, 35.7, 34.7, 33.1, 33.0, 30.9, 30.4, 29.2, 24.6, 23.0, 20.8, 20.7, 17.2, 16.7, 14.6.

EXAMPLE 3

Mo(N-2,6-Me$_2$ CH$_3$)(CHCMe$_2$Ph)[(−)-t-Bu$_2$Me Biphen] (2')

This complex was prepared in the same method as for Mo(N-2,6-i-Pr$_2$C$_6$H$_3$)(CHCMe$_2$Ph)-[(−)-t-Bu$_2$Me$_4$Biphen] with one exception. Dissolving the pentane extract in benzene and then removing the solvent under vacuum gave a red sponge which became a powder after crushing. The purity of this compound was confirmed by $^1$H NMR. $^1$H NMR (C$_6$D$_6$) δ 11.01 (s, 1H,=CHR), 7.39 (s, 1H, biph), 7.25 (d, 2H, Ph), 7.11 (s, 1H, biph), 7.05 (t, 2H, Ph), 6.88 (t, 1H, Ph), 6.63 (s, 3H, NAr'), 2.218 (s, 6H, Ar'Me$_2$), 2.101 (s, 3H, biph), 1.968 (s, 3H, biph), 1.720 (s, 3H, biph), 1.608 (s, 3H, biph), 1.562 (s, 3H, CMe$_2$Ph), 1.532 (s, 9H, t-Bu), 1.505 (s, 9H, t-Bu), 1.200 (s, 3H, CMe$_2$Ph). $^{13}$C{$^1$H} NMR (C$_6$D$_6$) 6 278.94 (d, J$_{CH}$=120.6 Hz), 155.97, 155.10, 154.18, 150.94, 140.16, 138.28, 137.16, 136.82, 135.65, 132.10, 131.04, 130.91, 130.82, 130.47, 130.05, 128.51, 128.31, 127.38, 127.25, 236.35, 54.16, 36.00, 35.76, 32.83, 31.93, 30.92, 30.56, 20.84, 20.73, 19.80, 17.34, 16.82.

EXAMPLE 4

Conditions for the Kinetic Resolution of 4-triethylsilvloxide-5-methyl-1,6-octadiene (3)

Both 2 and 2' efficiently ring-close the substrate, 3-methyl-4-triethylsiloxide-2.7-diene (3), over several hours (eq 5). As an example, the optically active catalyst 2 (73 mg, 0.0984 mmol,

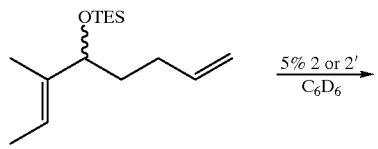

(5)

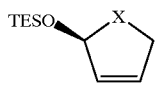

5%) was dissolved in toluene (20 mL). The substrate 3 was then added and the flask sealed with a plastic cap. After a period of time (1.5 or 23 hours), the reaction was opened to air and methanol added (1 mL). The volatile compounds were removed on a rotary evaporator and the resulting liquid was passed through an alumina plug with ether. The ether was removed affording a yellow liquid (470 mg, 95% mass conservation: assuming 50% conversion and all biphenH$_2$). The percent conversion was determined by integration of $^1$H NMR (500 MHZ, CDCl$_3$) signals: starting material (3.9 ppm) and ring-closed product (average of 4.6 and 5.45 ppm). Full NMR data for 3 has been reported in the literature. The ring-closed product is separated from 3 and BiphenH$_2$ (1) by column chromatography on silica with 100% hexane gradually shifting to 10% CH$_2$Cl$_2$ in hexane. The diene and 1 (198 mg) and ring-closed product (170 mg) were collected separately. On standing overnight, 1 crystallized from resolved 3 and was recycled. The triethylsilyl group is removed by treatment with fluoride ion in wet tetrahydrofuran.

Figure 2:
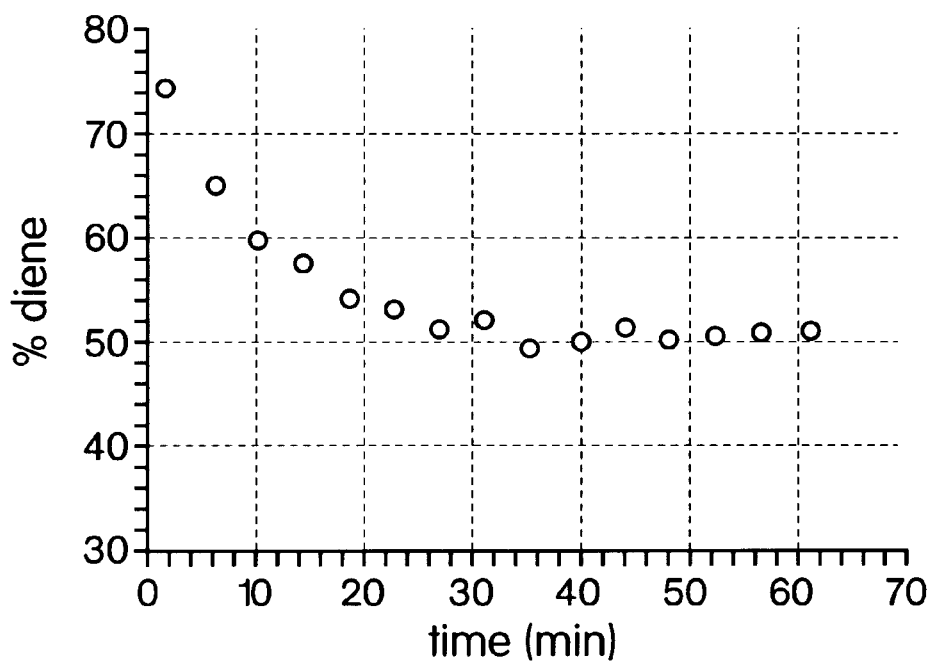
FIG. 2 shows a consumption plot in the reaction of the substrate 4-triethylsilyloxide-5-methyl-1,6-octadiene (3) with one enantiomer of $Mo(N-2,6-i-Pr_2C_6H_3)(CHCMe_2Ph)$ $[(-)-t-Bu_2Me_4Biphen]$ (2).

The consumption plot of 3, with 5% 2 obtained with the PAD(1) NMR macro (300 MHZ), shows 50% conversion of starting material over 30 minutes and then no further significant conversion during the next half hour (FIG. 2). After 17 hours, the reaction is 57% complete. This indicates that the relative rate, S, is greater that 25.

Both diene and cyclopentene were then deprotected and derivatized. The diene (148 mg, 0.58 mmol) was added neat to a THF (5 mL) solution of [n-Bu$_4$NF]OH$_2$ (1.03 eq, 0.6 mmol, 167 mg). After stirring for 90 minutes at room temperature, the reaction was concentrated on a rotary evaporator and slurried in ether (10 mL). The solution was sequentially washed with water and brine and dried over MgSO$_4$. The purity of the isolated alcohol was confirmed by $^1$HNMR and compared favorably with the literature.

The free alcohols are purified and treated with Mosher's acid chloride in pyridine to form a mixture of diastereomeric esters. A fraction of isolated alcohol (17 mg, 0.122 mmol) was dissolved in dry pyridine (2 mL). Neat Mosher's acid chloride (1.3 eq, 40 mg, 0.158 mmol) was added the mixture was allowed to stand overnight. The reaction was added dropwise onto ice water and extracted with ether (2×10 mL). The ether extracts were washed with water (4×10 mL) and brine (2×10 mL) and then dried with MgSO$_4$. Enantiomeric excess was determined by examining the trisubstituted olefinic resonances (both diene and ring-closed product) by 500 MHZ $^1$H NMR. For the diene these resonances appeared at 5.64 and 5.56 ppm. In the ring-closed product the olefinic resonances are observed at 5.70/5.67 and 3.57/3.56 ppm (OMe in R*). The kinetic resolution was quenched at 90 minutes and 23 hours. The percent conversion and determined % e.e. are tabulated in Table 1. With the two data points the S value for this system is approximately 25.

TABLE 1

| Kinetic resolution of 3 with 2 | | | |
|---|---|---|---|
| Time (h) | Conversion (%) | % e.e. diene | % e.e. RCM |
| 1.5 | 50.6 | 84.7 | 70.6 |
| 23 | 55.3 | 87.8 | 62.0 |

Those skilled in the art would readily appreciate that all parameters listed herein are meant to be exemplary and that actual parameters will depend upon the specific application

What is claimed is:

1. A composition comprising:

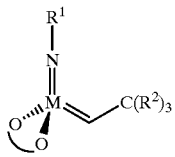

wherein M is a metal ion; $R^1$ and $R^2$ can be the same or different and each of the three $R^2$ groups can be the same or different, and each is selected from the group consisting $C_1$–$C_{12}$ alkyl, heteroalkyl, aryl, heteroaryl and adamantyl; and

is a chiral dialkoxide of at least 80% optical purity, the dialkoxide having sufficient rigidity such that a

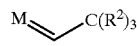

reaction site is of sufficient shape specificity, defined in part by the dialkoxide and a M=N—$R^1$ site to cause a mixture of two enantiomeric olefins to react with a M=C center at the

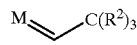

reaction site at different rates forming a catalytic olefin metathesis product that has at least a 50% enantiomeric excess of one enantiomer present in the mixture.

2. A composition as in claim 1, wherein the dialkoxide comprises two linked oxygen atoms such that a group of atoms defining the shortest chemical bond pathway between the two oxygen atoms has at least four atoms.

3. A composition as in claim 1, wherein

comprises the structure:

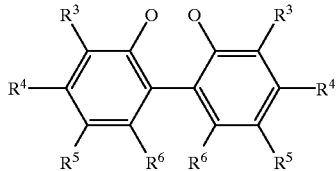

wherein $R^3$–$R^6$ can be the same or different, and each is selected from the group consisting of hydrogen, alkyl, alkenyl, alkynyl, cycloalkyl, cycloalkenyl, cycloalkynyl, aryl, alkaryl, aralkyl and optionally interrupted or terminated by N, O, P, S, heteroalkyl, heteroaryl, carbonyl, acyl, acyloxy, —CHO, —COOR$^7$, —CO$_2$C(R$^7$)$_3$, —CONC(R$^7$)$_2$, cyano, NO$_2$, alkyloxy, aryloxy, hydroxy, hydroxyalkyl, amino, alkylamino, dialkylamino, arylamino, diarylamino, —NR$^7$COR$^8$, thioalkyl, thioaryl, —SO$_2$R$^7$, —SOR$^7$, —SO$_2$OR$^7$, F, Cl, Br, I; R$^7$ and R$^8$ can be the same or different, and each is selected from the group consisting of hydrogen, $C_1$–$C_{12}$ alkyl, $C_1$–$C_{12}$ heteroalkyl, aryl, heteroaryl, hydroxyl, F, Cl, Br and I; and any two R groups where possible can combine to form a closed ring system selected from the group consisting of aryl, heteroaryl, substituted aryl, biaryls, and substituted biaryls.

4. A composition as in claim 3, wherein $R^3$–$R^6$ can be the same or different and each is selected from the group consisting of $C_1$–$C_{12}$ alkyl, heteroalkyl, aryl, heteroaryl, optionally interrupted or terminated by N or O, and any two R groups where possible can combine to form a closed ring system selected from the group consisting of aryl, heteroaryl, substituted aryl, biaryls and substituted biaryls.

5. A composition as in claim 3, wherein $R^3$ is selected from the group consisting of i-propyl, t-butyl, cyclohexyl and t-octyl, $R^4$ is selected from the group consisting of hydrogen and $C_1$–$C_2$ alkyl, $R^5$ is selected from the group consisting of hydrogen and $C_1$–$C_2$ alkyl, and $R^6$ is methyl.

6. A composition as in claim 1 wherein $R^1$ is selected from the group consisting of 2,6-dimethylphenyl, 2,6-diethylphenyl and 2,6-diisopropylphenyl and $R^2$ is selected from the group consisting of methyl, ethyl and phenyl.

7. A composition as in claim 1, wherein M is molybdenum or tungsten.

8. A composition as in claim 1, wherein the composition is at least 80% optically pure.

9. A composition as in claim 1, wherein the composition is at least 90% optically pure.

10. A composition as in claim 1, wherein the composition is at least 95% optically pure.

11. A composition as in claim 1, wherein the composition is at least 99% optically pure.

12. A composition as in claim 11, which, when exposed to a diene source results in catalytic conversion to a ring-closed compound.

13. A composition as in claim 12, which, when exposed to the diene source comprising a racemic diene mixture forms a ring-closed compound having an enantiomeric excess of at least 50% at 50% conversion of the racemic diene mixture.

14. A composition as in claim 12, which, when exposed to the diene source comprising a racemic diene mixture forms a ring-closed compound having an enantiomeric excess of at least 85% at 50% conversion of the racemic diene mixture.

15. A composition as in claim 12, which, when exposed to the diene source comprising a racemic diene mixture forms a ring-closed compound having an enantiomeric excess of at least 90% at 50% conversion of the racemic diene mixture.

16. A composition as in claim 12, which, when exposed to the diene source comprising a racemic diene mixture forms a ring-closed compound having an enantiomeric excess of at least 95% at 50% conversion of the racemic diene mixture.

17. A composition as in claim 12, which, when exposed to the diene source comprising a racemic diene mixture, forms a ring-closed compound and an unreacted amount of the diene source has an enantiomeric excess of at least 50% at 50% conversion of the racemic diene mixture.

18. A composition as in claim 12, which, when exposed to the diene source comprising a racemic diene mixture, forms a ring-closed compound and an unreacted amount of the diene source has an enantiomeric excess of at least 85% at 50% conversion of the racemic diene mixture.

19. A method comprising providing a composition of claim 1 and reacting the composition with a diene.

20. A method comprising:

reacting a diene mixture including a mixture of enantiomers with a composition of the structure:

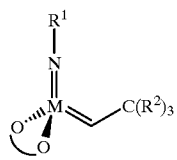

and allowing a first enantiomer of the mixture to metathesize at M to an extent greater than a second enantiomer of the mixture such that a product is formed from the diene mixture that has an enantiomeric excess of at least 50%, wherein M is a metal ion; $R^1$ and $R^2$ can be the same or different and each of the three $R^2$ groups can be the same or different, and each is selected from the group consisting $C_1$–$C_{12}$ alkyl, heteroalkyl, aryl, heteroaryl and adamantyl; and

is a chiral dialkoxide of at least 80% optical purity.

21. A method as in claim 20, wherein the composition is at least 80% optically pure.

22. A method as in claim 20, wherein the composition is at least 90% optically pure.

23. A method as in claim 20, wherein the composition is at least 95% optically pure.

24. A method as in claim 20, wherein the composition is at least 99% optically pure.

25. A method as in claim 20, wherein the step of adding the diene mixture to the composition produces a ring-closed compound catalytically.

26. A method as in claim 20, wherein the diene mixture comprises the structure:

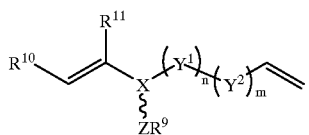

wherein X is selected from the group consisting of $CR^{12}$, N or P; $Y^1$, $Y^2$ and Z are selected from the group consisting of $CR^{12}R^{13}$, $NR^{12}$, O or S and $R^{10}$ and $R^{11}$ can be the same or different, and each is selected from the group consisting of hydrogen, alkyl, alkenyl, alkynyl, cycloalkyl, cycloalkenyl, cycloalkynyl, aryl, alkaryl, aralkyl and optionally interrupted or terminated by N, O, P, S, heteroalkyl, heteroaryl, carbonyl, acyl, acyloxy, —CHO, $OOR^{12}$, —$CO_2C(R^{12})_3$, —$CONC(R^{12})_2$, cyano, $NO_2$, alkyloxy, aryloxy, hydroxy, hydroxyalkyl, amino, alkylamino, dialkylamino, arylamino, diarylamino, —$NR^{12}COR^{13}$, thioalkyl, thioaryl, —$SO_2R^{12}$, —$SOR^{12}$, —$SO_2OR^{12}$, F, Cl, Br, I; $R^9$, $R^{12}$ and $R^{13}$ can be the same or different, and each is selected from the group consisting of hydrogen, $C_1$–$C_{12}$ alkyl, $C_1$–$C_{12}$ heteroalkyl, aryl, heteroaryl, hydroxyl, alkylsilyl, arylsilyl, alkarylsilyl, F, Cl, Br and I; and any two R groups where possible can combine to form a closed ring system selected from the group consisting of aryl, heteroaryl, substituted aryl, biaryls, and substituted biaryls.

27. A method as in claim 26, wherein $Y^1$, $Y^2$ and Z can be the same or different and each is selected from the group consisting of $CR^{12}R^{13}$, $NR^{12}$, O or S; $R^{10}$, $R^{11}$, $R^{12}$ and $R^{13}$ can be the same or different and each is selected from the group consisting of $C_1$–$C_{12}$ alkyl, heteroalkyl, aryl or substituted aryl and $R^9$ is selected from the group consisting $C_1$–$C_{12}$ alkyl, heteroalkyl, aryl or substituted aryl, alkylsilyl, arylsilyl, and alkylarylsilyl.

28. A method as in claim 26, wherein X is CH, $Y^1$ and $Y^2$ each are $CH_2$, and $ZR^9$ is selected from the group consisting of acetate, t-butylacetate, trifluoroacetate, and trialkylsilyloxide.

29. A method as in claim 26, wherein n+m is at least 2.

30. A method as in claim 26, wherein n+m=2 to 4.

31. A method as in claim 26, wherein n+m=2.

32. A method as in claim 26, wherein the step of adding the diene mixture to the composition produces a ring-closed metathesis compound having an enantiomeric excess of at least 50% at 50% conversion of the racemic diene mixture.

33. A method as in claim 26, wherein the step of adding the diene mixture to the composition produces a ring-closed metathesis compound having an enantiomeric excess of at least 85% at 50% conversion of the racemic diene mixture.

34. A method as in claim 26, wherein the step of adding the diene mixture to the composition produces a ring-closed metathesis compound having an enantiomeric excess of at least 90% at 50% conversion of the racemic diene mixture.

35. A method as in claim 26, wherein the step of adding the diene mixture to the composition produces a ring-closed metathesis compound having an enantiomeric excess of at least 95% at 50% conversion of the racemic diene mixture.

36. A method as in claim 26, wherein the step of adding the diene mixture to the composition produces a ring-closed metathesis compound such that an unreacted amount of diene has an enantiomeric excess of at least 50% at 50% conversion of the racemic diene mixture.

37. A method as in claim 26, wherein the step of adding the diene mixture to the composition produces a ring-closed metathesis compound such that an unreacted amount of diene has an enantiomeric excess of at least 85% at 50% conversion of the racemic diene mixture.

38. A method as in claim 26, wherein the step of adding the diene mixture achieves 50% conversion within a time of at least 5 minutes.

39. A method as in claim 26, whereupon adding the diene mixture to the composition, one enantiomer reacts more rapidly than the other enantiomer such that S (=$k_r/k_s$) is at least 10.

40. A method as in claim 26, whereupon adding the diene mixture to the composition, one enantiomer reacts more rapidly than the other enantiomer such that S (=$k_r/k_s$) is at least 25.

* * * * *

UNITED STATES PATENT AND TRADEMARK OFFICE
CERTIFICATE OF CORRECTION

PATENT NO. : 6,121,473
DATED : September 19, 2000
INVENTOR(S) : Richard R. Schrock et al.

It is certified that error appears in the above-identified patent and that said Letters Patent is hereby corrected as shown below:

Column 15, line 62, "OOR$^{12}$" should be --COOR$^{12}$--.

Signed and Sealed this

Twenty-fourth Day of April, 2001

Attest:

NICHOLAS P. GODICI

Attesting Officer      Acting Director of the United States Patent and Trademark Office